United States Patent [19]

Olson et al.

[11] Patent Number: 4,889,806

[45] Date of Patent: Dec. 26, 1989

[54] LARGE DNA CLONING SYSTEM BASED ON YEAST ARTIFICIAL CHROMOSOMES

[75] Inventors: Maynard V. Olson; David T. Burke, both of St. Louis, Mo.

[73] Assignee: Washington University, St. Louis, Mo.

[21] Appl. No.: 38,280

[22] Filed: Apr. 15, 1987

[51] Int. Cl.$^4$ .................. C12N 15/00; C12N 5/00; C12N 7/00

[52] U.S. Cl. .................. 435/172.3; 435/255; 435/256; 435/320; 435/912; 435/69.2; 435/9.4; 935/28; 935/55; 935/56; 935/67

[58] Field of Search .................. 435/172.3, 256, 320, 435/317.1, 942; 935/28, 55, 56, 69

[56] References Cited

PUBLICATIONS

Murray and Szostak, Nature 305, 189–193, (1983).
Hieter et al., Cell 40, 381–392, (1985).
Murray et al., Cell 45, 529–536, (1986).
Surosky et al., Proc. Natl. Acad. Sci. USA 83, 414–418, (1986).
Mann and Davis, Mol. Cell. Biol. 6, 241–245, (1986).
Stinchcomb et al., Nature 282, 39–43, (1979).
Tschumper and Carbon, Gene 10, 157–166, (1980).
Rose et al., Gene 29, 113–124, (1984).
Szostak and Blackburn, Cell 29, 245–255, (1982).
Dunn et al., Cell 39, m 191–201, (1984).
Struhl, Proc. Natl. Acad. Sci. USA, 79, 7385–7389, (1982).
Goodman et al., Proc. Natl. Acad. Sci. USA, 74, 5453–7, (1977).
Shaw and Olson, Mol. Cell. Biol. 4, 657–665, (1984).
Burke, D. T. et al; Construction of Large Linear Plasmid Library From Higher Eucaryote Genones; J. Cell Biochem. Suppl. (11B), (1987).
Hieter et al; A Colony Color Assay that Measures Mitotic Stability of Yeast Chromozones: Non—disjunction and Chromosome Loss; Cell 40, pp. 381–392, (1985).
Surosky, R. J. et al; The Mitotic Stability of Deletion Derivatives of Chromosome III in Yeast; Proc. Natl. Acad. Sci. 83, pp. 414–418, (1986).
Murray, A. W. et al.; Chromosome Length Controls Mitotic Chromosome Segregation in Yeast; Cell 45, pp. 529–536, (1986).

*Primary Examiner*—Robin Teskin
*Attorney, Agent, or Firm*—Scott J. Meyer; James W. Williams, Jr.

[57] ABSTRACT

A large DNA cloning system is disclosed which is based on yeast artificial chromosomes. Cloning vectors are disclosed which allow the cloning of large segments of greater than 50 kb of exogenous DNA. The cloning vector comprises DNA sequences of an autonomous replication sequence, a centromere, a selectable yeast marker, two sequences that seed telomere function in vivo, and a cloning site within an interruptible yeast gene for insertion of the exogenous DNA segments.

21 Claims, 7 Drawing Sheets

FIG. I.

FIG. 2C total human probe

FIG. 2B pBR322 probe

FIG. 2A EtBr stained gel

Et Br stained gel

FIG. 3A.

FIG. 3B — pBR 322 probe

FIG. 3C — total human probe

total human probe

FIG. 7.

LARGE DNA CLONING SYSTEM BASED ON YEAST ARTIFICIAL CHROMOSOMES

BACKGROUND OF THE INVENTION

This invention relates to a large DNA cloning system and, more particularly, to vectors that allow the cloning of large segments of exogenous deoxyribonucleic acid (DNA) as yeast artificial chromosomes.

The baker's yeast *Saccharomyces cerevisiae* is one of the most useful eukaryotic organisms in the field of molecular biology. It has a small genome or DNA content only about 3 times that of *E. coli*, a short generation time of a few hours and it is as readily manipulated as most procaryotes, yet it exhibits some very complex phenomena specific to eukaryotes such as chromosome structure, mitotic and meiotic cell division.

With the advent of recombinant DNA and molecular cloning technology, it is now possible to transfer genetic information from any source into microorganisms, including yeasts. Using conventional recombinant DNA techniques, small plasmid and viral chromosomes can be constructed in vitro and then transferred into host cells and clonally propagated.

Most DNA cloning systems have a capacity only for relatively small segments of exogenous DNA, for example, on the order of up to about 50 kilobases (kb), and bacterial clones such as *E. coli* are frequently unstable. These cloning systems are well suited to the analysis and manipulation of typical genes and small gene clusters, particularly from organisms in which the genetic information is tightly packed. It is increasingly apparent, however, that many of the functional genetic units in higher organisms span enormous tracts of DNA. For example, the bithorax locus in Drosphila, which is involved in regulating the development of the fly's segmentation pattern, encompasses approximately 320 kb [Karch et al., *Cell* 43, 81 (1985)]. The factor VIII gene in the human, which encodes the blood-clotting factor deficient in hemophilia A, spans 190 kb [Gitschier et al., *Nature* 312, 326 (1984)]. Recent estimates of the size of the gene that is defective in Duchenne's muscular dystrophy suggest that this single genetic locus, whose protein-coding function could be fulfilled by as little as 15 kb of DNA, actually covers more than a million base pairs [Monaco et al., *Nature* 323, 646 (1986)].

It is thus seen that a DNA cloning system that allows the cloning of large segments of exogenous DNA, on the order of greater than 50 kb, would have significant utility.

Although techniques exist for cloning large genes or gene clusters in many overlapping, relatively small pieces, this process is laborious, error-prone, and poorly suited to functional studies of the cloned DNA. Furthermore, there are a number of problems in molecular genetics that will require the characterization of even more extensive tracts of DNA than those present in the largest known genes. For example, the regulated somatic DNA rearrangements that give rise to functional immunoglobulin and T-cell-receptor genes involve deletions of whole segments of chromosomes, while some of the genetic events that have been implicated in the induction or progression of malignant tumors involve the amplification of similarly large regions. See Tonegawa, *Nature* 302, 575 (1985); Kronenberg et al., *Ann. Rev. Immuno.* 4, 529 (1986); and Bishop, *Science* 235, 305 (1987). In other instances, including efforts to define the primary defects in such genetic diseases as Huntington's chorea and cystic fibrosis, only the genetic linkage between the closest identified clones and the disease locus is known. See Beaudet et al., *Am. J. Hum. Genet.* 39, 681 (1986), and Gusella et al., *Nature* 306, 234 (1983). In typical cases, the search for the locus itself will require the analysis of megabase-pair regions of DNA. Mapping of these large regions of DNA can lead to the cloning of candidate genes. Isolation of the aberrant gene will facilitate development of better markers and probes for the gene and this, in turn, can result in diagnostic tests for the genetic disease. Ultimately, isolation and characterization of the defective gene can lead to the development of therapeutic interventions.

Finally, there is increasing interest in the global mapping of the DNA of intensively studied organisms. See Olson et al., *Proc. Natl. Acad. Sci. USA* 83, 7826 (1986), and Coulson et al., Ibid., 83, 7821 (1986). See also the reports of discussions by the National Academy of Sciences to map and sequence the human genome in *Science* 235, 747-748 (1987). Particularly in the case of the human, or other organisms with comparably complex genomes, such projects would require the ordering of hundreds of thousands of conventional clones. A cloning system that allowed the same objective to be achieved with many fewer clones would not only improve mapping efficiency, but it would also have dramatic effects on the reliability and continuity of the final map.

BRIEF DESCRIPTION OF THE INVENTION

In accordance with the present invention, a large DNA cloning system has been developed which is based on yeast artificial chromosomes. Unique vectors are provided herewith which allow the cloning of large segments of greater than 50 kb of exogenous DNA as yeast artificial chromosomes. This high capacity cloning system is based on the in vitro construction of linear DNA molecules that can be transferred into yeast where they are maintained as artificial chromosomes.

The yeast artificial chromosomal vectors are provided with the following structural components for replication in yeast: a centromere (CEN), telomeres (TEL), autonomous replication sequence (ARS), yeast selectable markers, and a cloning site for insertion of large segments of greater than 50 kb of exogenous DNA. Preferably, yeast selectable markers are carried on both sides of the centromere, and two sequences that seed telomere formation in vivo are separated by a throw-away sequence. These components are defined as follows:

The centromere is that part or region of the yeast chromosome that controls movement of the chromosome during cell division. Centromeres stabilize the mitotic and meiotic transmission of circular and linear plasmids.

Telomeres are the ends of the chromosome that allow stable maintenance and replication of the ends of linear DNA molecules in yeast.

The autonomous replication sequence is a DNA segment that allows replication of the yeast independently of the yeast chromosome. It confers on the plasmid the ability to replicate extrachromosomally.

Selectable markers are wild-type alleles of genes that encode biosynthetic enzymes. Yeast genes coding for biosynthetic enzymes in, for example, the tryptophan, histidine and uracil pathways (namely, TRP1, HIS3 and URA3, respectively) can be used as convenient selectable markers in a suitable auxotrophic yeast strain.

The throw-away sequence is a DNA segment that separates the telomeres in a circular plasmid which is discarded upon cleaving the plasmid to form linear DNA molecules.

The cloning site is provided in an interruptible yeast gene marker whose interruption is phenotypically visible.

Most of the foregoing basic structural components of yeast have been employed heretofore in artificial chromosomes that are about 50 kb or somewhat larger. See Murray and Szostak, Nature 305, 189–193 (1983); Hieter et al., Cell 40, 381–392 (1985); Murray et al., Cell 45, 529–536 (1986); and Surosky et al., Proc. Natl. Acad. Sci. USA 83, 414–418 (1986). However, according to these prior reports the gene clusters are cloned in many overlapping, relatively small pieces rather than in large DNA segments as defined herein. That is, the prior studies of yeast artificial chromosomes have been carried out on molecules that formed in vivo by recombination between very small linear plasmids and transforming DNA. Typically, the linear plasmid contained all sequences required for replication and segregation, while the transforming DNA contained a marker that would be used to select for the recombinant molecule. Although such systems allow artificial chromosomes to be custom-tailored for genetic studies, they are poorly suited to cloning applications. In contrast, the system defined herein employs in vitro ligation of vector and source-DNA fragments followed by transformation of the intact replicons into host cells.

The yeast DNA cloning system vectors of the present invention preferably also contain DNA sequences that allow replication in bacteria such as E. coli. Inclusion in the plasmid of those portions of plasmid pBR322 with the ampicillin resistance gene (Amp) and the E. coli origin of replication (ori) permit selective and stable growth in E. coli. The vectors thus can be shuttled back and forth between yeast and bacterial organisms.

The vectors, or plasmids, of the present invention are defined herein as Yeast Artificial Chromosome (YAC) vectors.

DETAILED DESCRIPTION OF THE INVENTION

While the specification concludes with claims particularly pointing out and distinctly claiming the subject matter regarded as forming the present invention, it is believed that the invention will be better understood from the following description of preferred embodiments taken in connection with the accompanying drawings in which briefly:

Plasmids pYAC2 and pYAC4 are on deposit without restriction at the American Type Culture Collection, Rockville, Md., under accession numbers ATCC 67380 and ATCC 67379, respectively. Saccharomyces cerevisiae strain AB1380 is similarly on deposit without restriction at said depository under accession number ATCC 20843.

The preferred embodiments of the invention described herein employ the use of a number of commonly available restriction endonucleases which are identified below with their corresponding recognition sequences and (indicated by arrow) cleavage patterns. The letters A, T, G and C connote the nucleotides containing the bases adenine, thymine, guanine and cytosine, respectively, while N connotes any of these nucleotides, Pu connotes purine base and Py connotes pyrimidine base. Other well-known restriction endonucleases can be selected for use in the invention for cleaving DNA at specific base sequences as may be desired.

| | | | | |
|---|---|---|---|---|
| BamH I | GGATCC↓<br>CCTAAG↑ | | EcoR I | GAATTC↓<br>CTTAAG↑ |
| Sma I | CCCGGG↓<br>GGGCCC↑ | | Pvu II | CAGCTG↓<br>GTCGAC↑ |
| Xho I | CTCGAG↓<br>GAGCTC↑ | | Alu I | AGCT↓<br>TCGA↑ |
| SnaB I | TACGTA↓<br>ATGCAT↑ | | Kpn I | GGTACC↓<br>CCATGG↑ |
| Sfi I | GGCCNNNNNGGCC↓<br>CCGGNNNNNCCGG↑ | | Ava I | CPyCGPuG↓<br>GPuGCPyC↑ |
| Not I | GCGGCCGC↓<br>CGCCGGCG↑ | | | |

Figure 1:
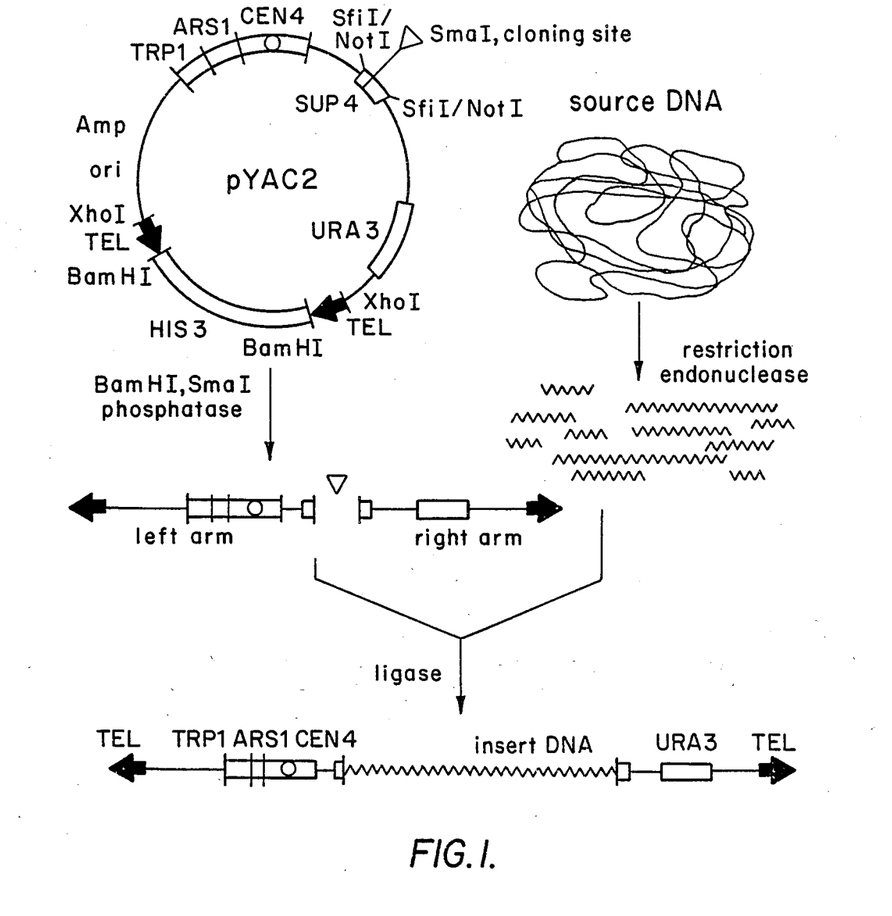
FIG. 1 is a diagrammatic representation which shows the yeast plasmid vector pYAC2 and its use in the construction of a linear yeast artificial chromosome (YAC) in one embodiment of the invention.

In the illustrative plasmid, pYAC2, of FIG. 1, the structural components include a centromere (CEN4) as described by Mann and Davis, Mol. Cell. Biol. 6, 241–245 (1986); an autonomous replication sequence (ARS1) as described by Stinchcomb et al., Nature 282, 39–43 (1979); selectable markers on both sides of the centromere, namely TRP1 as described by Tschumper and Carbon, Gene 10, 157–166 (1980); and URA3 as described by Rose et al., Gene 29, 113–124 (1984); two sequences that seed telomere formation in vivo (labeled TEL) as described by Szostak and Blackburn, Cell 29, 245-255 (1982), Dunn et al., *Cell* 39, 191-201 (1984), and Murray et al., *Cell* 45, 529-536 (1986); HIS3 as described by Struhl *Proc. Natl. Acad. Sci. U.S.A.*, 79, 7385-7389 (1982), which serves as a throw-away segment whose absence can be verified genetically in transformants, thereby allowing some anomalous molecules to be screened out; and a cloning site within a gene whose interruption is phenotypically visible (SUP4) as described by Goodman et al., *Proc. Natl. Acad. Sci. U.S.A.* 74, 5453-5457 (1977). As known from Murray et al., supra, cleavage at the BamH 1 sites adjacent to the TEL sequences produces termini that heal into functional telomeres in vivo.

The illustrative plasmid pYAC2 also contains most of the DNA of the *E. coli* plasmid pBR322, which is a standard plasmid first described by Bolivar et al., *Gene* 2, 95-113 (1977). This is a well-known, commercially available plasmid whose restriction endonuclease map was first published by Sutcliffe, *Nucleic Acids Res.* 5, 2721-2728 (1978). pBR322 has been constructed in vitro from the tetracycline resistance gene (Tc) from pSC101, the origin of DNA replicon (ori) from the colE1 derivative pMB1, and the ampicillin resistance gene (Amp) from transposon Tn3. The ori from pBR322 allows replication of plasmid pYAC2 in *E. coli* and is useful in recovering sequences from the yeast artificial chromosomes in a plasmid rescue scheme as described hereinafter.

The cloning site in pYAC2 is the Sma I site in the SUP4 gene. SUP4 is a desirable interruptible marker because the intact gene confers a colony-color phenotype in appropriate host strains as seen from Shaw and Olson, *Mol. Cell. Biol.* 4, 657-665 (1984). The gene can also be selected for or against using standard genetic methods as described by Kurjan and Hall, Ibid. 2, 1501-1513 (1982). These properties allow convenient screening and selective methods for eliminating non-recombinant transformants that have simply religated at the cloning site without incorporation of an insert.

The preferred overall scheme of the cloning system is shown in FIG. 1. Double digestion of the particular YAC vector shown, pYAC2, with BamH I and Sma I yields three parts, which can be regarded as a left chromosome arm, including the centromere, a right chromosome arm, and a throwaway region that separates the two TEL sequences in the circular plasmid. The two arms are treated with alkaline phosphatase to prevent religation, and then ligated onto large insert molecules of greater than 50 kb derived from the source DNA by partial or complete digestion with an enzyme that leaves Sma I-compatible (i.e. blunt) ends. The ligation can be carried out with a DNA ligase such as T4-DNA ligase. The ligation products are then transformed into yeast spheroplasts by essentially conventional methods, which involve embedding the transformed spheroplasts in soft agar on a selective medium. See, for example, Sherman et al., *Methods in Yeast Genetics*, Cold Spring Harbor Laboratory, N.Y., pp. 101-111C, 114-115 (1983), for conventional transformation methods.

Primary transformants are selected for complementation of a ura3 marker in the host by the URA3 gene on the vector. The transformants are screened for complementation of a host trp1 marker, which insures that the artificial chromosomes have derived both their arms from the vector, and for loss of expression of the ochre suppressor SUP4, which is interrupted by insertion of exogenous DNA at the Sma I cloning site, which is a naturally occurring restriction site in the region coding for SUP4's tRNA$^{Tyr}$ gene product. As already mentioned, above, SUP4 is a particularly advantageous interruptible marker since in an ade2-ochre host, cells that are expressing the suppressor form white colonies while those in which the suppressor has been inactivated form red colonies. See Rothstein, *Genetics* 85, 55 (1977). When desired, one can also select against non-recombinants using the canl-ochre marker in the host since cells expressing SUP4 are canavanine-sensitive, while those lacking suppression are canavanine-resistant.

In order to further demonstrate the invention, cloning tests were carried out using the vector pYAC2 as follows:

An initial test of the vector system involved cloning Sma I limit-digest fragments of yeast and human DNA into pYAC2. The limit-digest fragments produced by cleaving either of these DNA's with Sma I, which recognizes the sequence CCCGGG, are predominantly in the size range 20-200 kb. In the case of the human digest, the insert DNA was size-fractionated by velocity sedimentation to eliminate fragments smaller than 40 kb. Because a low cloning efficiency was anticipated, the ligation mixtures were carried out on a large scale (50 μg vector+25 μg insert in 200 μl).

The initial yeast-into-yeast test produced only a handful of transformants of the desired phenotype (ura+, trp+, ade−, can$^R$, red), but a high fraction of those obtained contained novel DNA molecules that behaved electrophoretically as linear DNA molecules in the size range 40-130 kb. Control tests indicated that the main reason for the low efficiency was that the host strain transformed somewhat weakly, even with conventional *E. coli*/yeast shuttle vectors. For the human-into-yeast test, a new host strain, AB1380, was employed with substantially improved results. When only half the ligation mixture was transformed into $5 \times 10^7$ cells, $1 \times 10^4$ ura+ transformants were obtained. In a sample of 48 randomly picked colonies, 28 had all the phenotypes of bona fide recombinants, while 16 contained artificial chromosomes large enough to detect on ethidium-bromide-stained pulsed-field gels (>40 kb). This sampling indicated that the test had an overall yield of 300 useable clones per microgram of insert DNA.

Figure 2A:
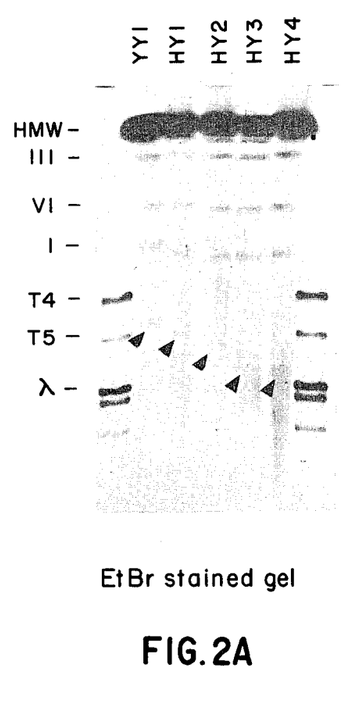
FIG. 2 shows the results of electrophoresis of 5 YAC clones derived from the pYAC2 plasmid of FIG. 1.
Figure 2B:
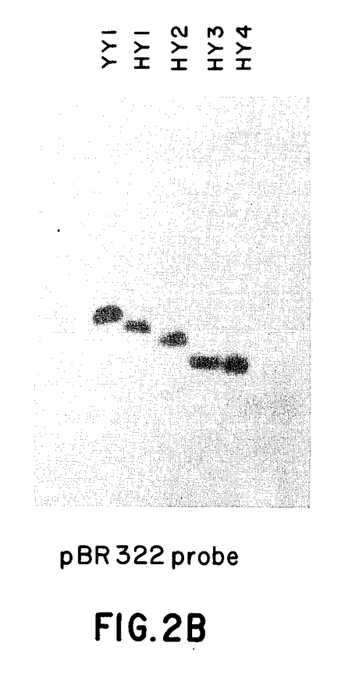
Figure 2C:
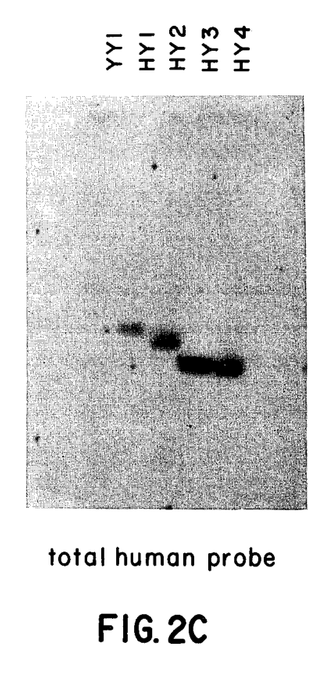

The structure of representative clones is shown as follows: A number of clones from the yeast/yeast and human/yeast initial tests were analyzed in more detail to determine whether or not the artificial chromosomes that had been produced had the proposed structures. FIG. 2 shows the analysis on a pulsed-field gel of one yeast/yeast and 4 human/yeast clones. The artificial chromosomes are visible on the ethidium-bromide-stained gel as 50-130 kb molecules, migrating ahead of the smallest natural yeast chromosomes (FIG. 2A). The DNA was transferred from this gel to nitrocellulose and assayed sequentially by DNA-DNA hybridization with $^{32}$P-labeled probes prepared from pBR322 (FIG. 2B) and total human genomic DNA (FIG. 2C). All 5 artificial chromosomes hybridized to pBR322, by way of the pBR322 sequences present in pYAC2. As seen, only the 4 human/yeast chromosomes hybridized to human DNA; under the hybridization conditions employed, the hybridization to total human DNA would involve primarily dispersed repetitive human sequences present both in the probe and in the cloned segments of human DNA. The absence of minor bands in FIG. 2, even when the autoradiograms are over-exposed, indicates that the yeast artificial chromosomes are propagated without changes in size.

Figure 3A:
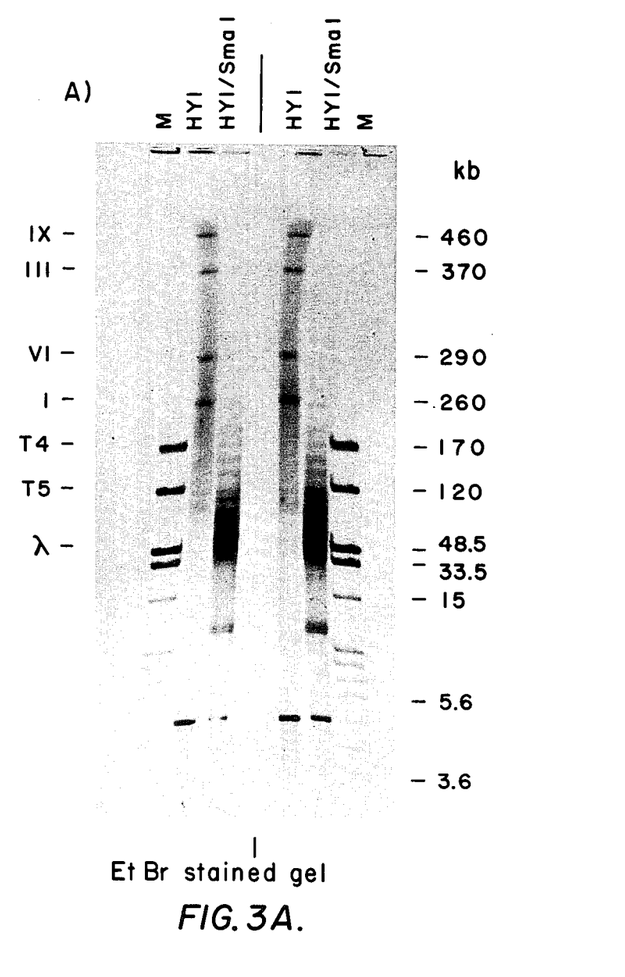
FIG. 3 shows the results of electrophoresis of a YAC human/yeast clone HY1 of FIG. 2, using the yeast host strain AB1380, demonstrating that the DNA insert is a single large Sma I fragment.

Further analysis of two of the larger artificial chromosomes, HY1 and YY1, demonstrated that both clones have the structure proposed for molecules formed by the simple pathway shown in FIG. 1. For example, the data in FIG. 3 demonstrate that the insert in HY1 can be released from vector sequences as a single 120-kb fragment by Sma I digestion. In FIG. 3A, an ethidium-bromide-stained gel is shown on which two sets of samples of uncleaved and Sma I-cleaved yeast DNA from the transformant containing HY1 have been fractionated on two identical half-gels. The DNA was transferred to nitrocellulose and the samples on the left were assayed with a pBR322 probe (FIG. 3B), while those on the right were assayed using a total-human probe (FIG. 3C). The pBR322 probe detects the intact artificial chromosome in the uncleaved sample but only the two short vector arms in the Sma I-cleaved sample. In contrast, while the total human probe again detects the intact chromosome in the uncleaved sample, it detects a single large fragment in the Sma I-cleaved sample, which is not significantly different in size from the intact chromosome. Similar results were obtained for YY1.

Figure 4A:
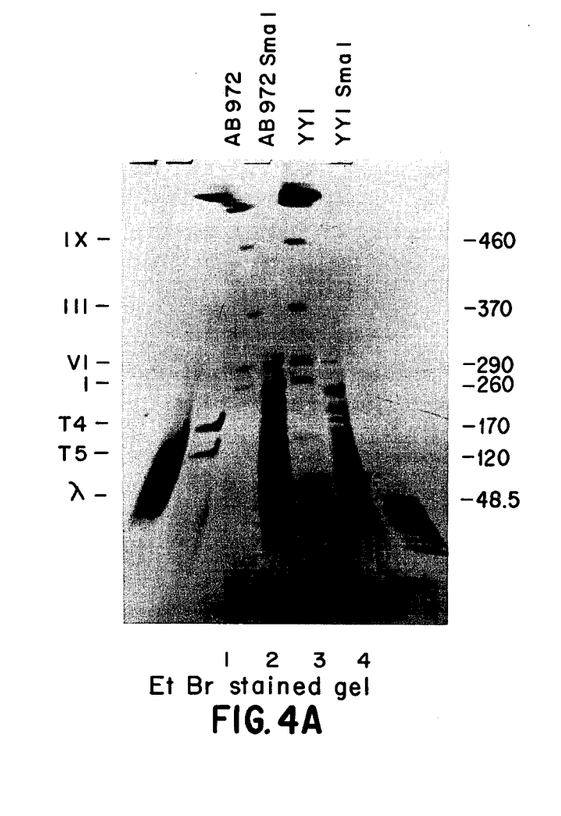
FIG. 4 shows the results of electrophoresis of a YAC yeast/yeast clone YY1 of FIG. 2 demonstrating that the large yeast Sma I fragment of the clone is also present in the genome of the source yeast.

A comparison of homologous cloned and genomic Sma I fragments is shown as follows: As a more stringent test of whether or not HY1 and YY1 represent authentic clones, it was also shown that the Sma I fragments clones in these artificial chromosomes are the same as homologous fragments in the source DNA. This test required the isolation of DNA fragments from the YAC inserts that could be used to probe size-fractionated Sma I digests of genomic human and yeast DNA. These fragments were isolated by a plasmid-rescue technique that takes advantage of the presence of pBR322 sequences in the original pYAC2 vector. The only Xho I sites in the pYAC2 vector are immediately centromere-proximal to the two TEL sequences (FIG. 1). Consequently, digestion of insert-containing artificial chromosomes would produce an Xho I fragment starting adjacent to the "left" TEL sequence and extending into the insert to the first Xho I site in the cloned DNA. Such a fragment would contain the pBR322 origin of replication and ampicillin-resistance gene (labeled ori and Amp in FIG. 1), which are the only portions of the plasmid that are essential for replication and selection in E. coli. In practice, plasmid rescue is a three-step procedure: total yeast DNA from transformants is digested with Xho I, ligated under conditions that favor formation of monomer circles, and transformed into E. coli with selection for ampicillin resistance. Plasmids with the proposed structures were readily isolated by this method from both YY1 and HY1. FIG. 4 illustrates the use of the YY1-derived plasmid to demonstrate that the large Sma I fragment cloned in this artificial chromosome has a counterpart in the source DNA. FIG. 4A shows an ethidium-bromide-stained gel on which uncleaved and Sma I-cleaved DNA was fractionated both from the yeast strain from which the source DNA was prepared (AB972) and from the YY1-transformed strain. When DNA was transferred from this gel and assayed by hybridization with the E. coli plasmid containing sequences rescued from YY1, the results confirmed that the Sma I fragment cloned into YY1 is of the same size in the clone and in genomic yeast DNA. In AB972, the probe hybridizes to a large chromosome in the uncleaved DNA (identified as chromosome XII in a separate test) and to a 120-kb fragment in the Sma I-cleaved DNA. In the sample containing uncleaved DNA from the transformed strain (lane 3), it hybridized both to the large natural chromosome and to the small artificial chromosome, while in the sample containing cleaved DNA from the transformed strain (lane 4), it hybridized only to the 120-kb Sma I fragment. In the latter sample, the band represents a direct superposition of homologous Sma I fragments released from the natural and artificial chromosomes. Similar tests were carried out using a probe rescued from HY1; the only discrete fragment to which this probe hybridized in Sma I digests of human DNA was of the correct size, but the probe also weakly cross-hybridized to a heterogeneous smear of smaller Sma I fragments.

Indirect-end-label mapping of YAC clones is shown as follows: With any primary cloning system, it is essential to have relatively simple methods of surveying the restriction sites present in newly isolated clones. Because of their large sizes, YAC clones are somewhat difficult to map by standard techniques. They are, however, well suited to indirect-end-label mapping, a method that has been employed for genomic sequencing and the mapping of hypersensitive sites in chromatin. See Church and Gilbert, *Proc. Natl. Acad. Sci. USA* 81, 1991 (1984), and Wu, *Nature* 286, 854 (1980). In indirect-end-label mapping, a partial digest of the chromosome is size-fractionated and then probed with a unique end-adjacent sequence, thereby revealing a ladder of bands, the sizes of which correspond to the distances from the end to the various cleavage sites for the restriction enzyme employed. YAC clones are particularly well suited to indirect-end-label mapping for three reasons: they have natural ends, the unique pBR322-derived sequences adjacent to each telomere allow redundant mapping of all clones using just two universal probes, and the need to detect partial-digest fragments that are present in much less than single-copy amounts is facilitated by the low sequence complexity of yeast DNA (0.5% of the mammalian case).

Figure 5:
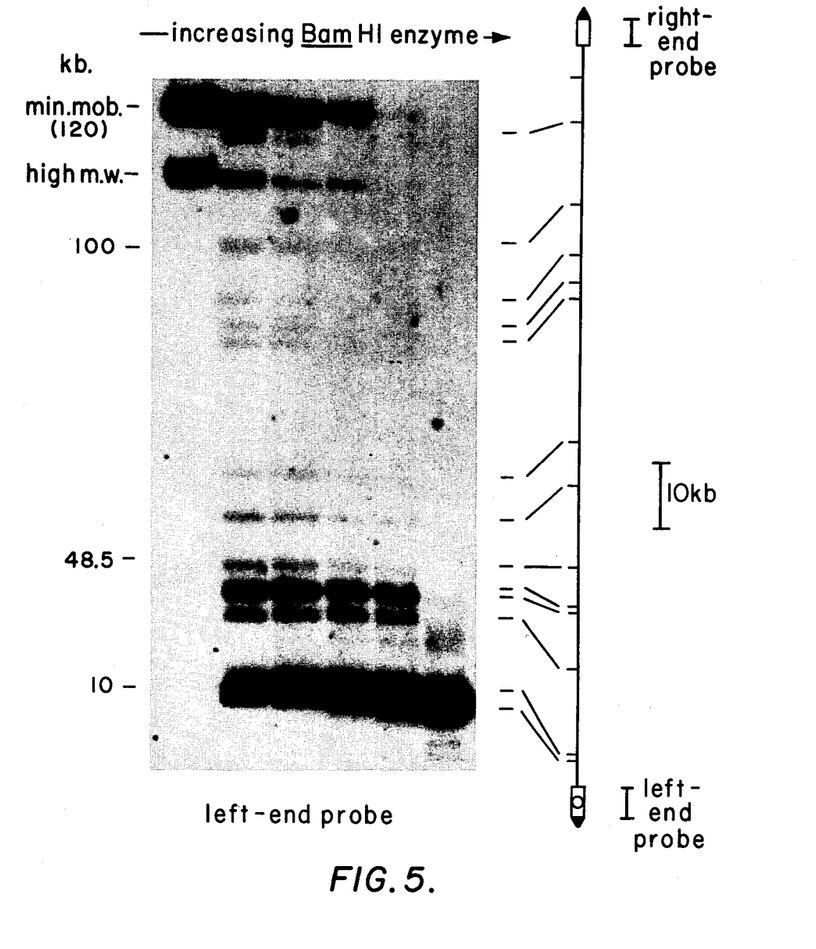
FIG. 5 shows the results of electrophoresis demonstrating the indirect-end-label mapping of the clone of FIG. 4 with BamH I.

FIG. 5 illustrates the indirect-end-label mapping of YY1 with Bam H1. Using just the left-end probe, all the sites for over a 100 kb could be mapped on a single high-resolution field-inversion gel. Complementary data were obtained using a right-end probe, which allowed completion of the map and also provided confirmation of the whole central region of the map. Although separate gels were employed in these tests, the two probes could equally well have been used sequentially on the same filter.

The following detailed examples will further illustrate the invention although it will be appreciated that the invention is not limited to these specific examples.

EXAMPLE 1

In this example, the plasmid vector pYAC2 was constructed and cloning tests were carried out with this vector as described in connection with the illustrative FIGS. 1 to 5 as follows:

As described above, FIG. 1 provides a schematic representation of the yeast-artificial-chromosome (YAC) cloning system. In the diagram of the vector, pYAC2, pBR322-derived sequences are shown as a thin line. SUP4, TRP1, HIS3, and URA3 are yeast genes: SUP4 is an ochre-suppressing allele of a tyrosine-tRNA gene that is interrupted when exogenous DNA is cloned into the vector; TRP1 and URA 3 are present in the artificial chromosomes and allow selection for molecules that have acquired both chromosome arms from the vector; HIS3 is discarded during the cloning process. ARS1 and CEN4 are sequences that are naturally adjacent to TRP1 on yeast's chromosome IV: ARS1 is an autonomous-replication sequence while CEN4 provides centromere function. The TEL sequences are derived from the termini of the Tetrahymena macronuclear rDNA molecules.

The vector was constructed in the following steps. The Sma I site in the URA3 gene of YIp5 [Struhl et al., *Proc. Natl. Acad. Sci. USA*, 76, 1035 (1979)] was deleted by digestion with Ava I followed by religation. In the isolate of YIp5 used herein, the Sma I site is flanked by two closely spaced Ava I sites, only one of which is predicted by the URA3 gene sequence. See Rose et al., *Gene* 29, 113 (1984). The resultant plasmid was cleaved at the unique Pvu II and EcoR I sites present in its pBR322-derived sequences [Sutcliffe, *Cold Spring Harbor Symp. Quant. Biol.* 43, 77 (1978)] and the EcoR I end was filled in with the Klenow fragment of DNA polymerase I [Jacobson et al., *Eur. J. Biochem.* 45, 623–627 (1974)] to produce a blunt-ended 3.2-kb fragment This fragment was ligated to a 5.5-kb fragment, containing TRP1, ARS1, and CEN4, which was produced by Pvu II cleavage of YCp19, a plasmid derived by Mann and Davis, *Mol. Cell. Biol.* 6, 241 (1986), by cloning a BamH I/EcoR I fragment from Sc4137 into the pBR322-derived sequences of YRp17. The resultant plasmid, pPM662, contains the regenerated Pvu II site of pBR322 and its adjacent replication origin and ampicillin-resistance genes, the TRP1/ARS1/CEN4 region of YCp19, and the URA3 gene of YIp5. The SUP4-o gene was cloned into the filled-in Bam H1 site of pPM662 on a 262-bp Alu I fragment derived from pSU4-A [Shaw and Olson, *Mol. Cell. Biol.* 4, 657 (1984)] by way of synthetic Sfi I/Not I linkers whose sequence was GCGGCCGCXGCGGCCGC (X=mixture of G and C); the resultant plasmid was named pPM664. A short portion of the CEN4 region of pPM664, containing an unwanted Xho I site, was deleted by digesting the plasmid at nearby unique sites for EcoR I and Kpn I, employing the Klenow fragment of DNA polymerase I to create blunt ends by filling in the 5' extension left by EcoR I and degrading the 3' extension left by Kpn I, and then religating. This procedure regenerated an unwanted, unique EcoR I site that was destroyed by cleavage with EcoR I, filling in, and religation to create pPM668. Finally, pYAC2 was created by inserting the TEL/HIS3/TEL Xho I fragment of A240p1 into the unique pBR322-derived Pvu II site of pPM668 by way of Xho I linkers; A240p1 was provided by A. W. Murray and contains the same TEL/HIS3/TEL module as the plasmids A252p6 [Dawson et al., *Science* 234, 713 (1986)] and A142p1 [Murray et al., *Cell* 45, 529 (1986)].

FIG. 2 provides a characterization of 5 YAC clones by pulsed-field gel electrophoresis. YY1 (Yeast/Yeast 1) is a clone containing yeast DNA cloned into yeast; the HY (Human/Yeast) clones contain human DNA cloned into yeast. (A) This panel shows an ethidium-bromide-stained pulsed-field gel of the transformants, in which the artificial chromosomes are visible as faint bands migrating ahead of chromosome I, which at 260 kb is the smallest natural yeast chromosome. See Schwartz and Cantor, *Cell* 37, 67 (1984), Carle and Olson, *Nucleic Acids Res.* 12, 5647 (1984) and *Proc. Natl. Acad. Sci. U.S.A.* 82, 3756 (1985), for electrophoresis procedure. The gel was run on a modified orthogonal-field-alternation gel electrophoresis (OFAGE) apparatus with a pulse time of 20 sec.; samples were prepared in agarose plugs, as described by Carle and Olson, *Ibid.* (B) This panel is an autoradiogram showing hybridization of all 5 clones to $^{32}$P-labeled pBR322 by way of vector-derived sequences. For this test, the DNA in the gel shown in (A) was transferred to a nitrocellulose sheet as described by Southern, *Methods Enzymol.* 68, 152 (1979); the probe was labeled by the hexamer-priming method of Feinberg and Vogelstein, *Anal. Biochem.* 137, 266 (1984). (C) This panel is an autoradiogram showing hybridization of only the four HY clones to $^{32}$P-labeled total-human DNA. For this test, the radioactivity associated with the pBR322 hybridization was stripped off the filter before re-hybridization with the total-human probe.

All the clones were produced by ligating pYAC-derived "arms" to source DNA that had been digested to completion with Sma I and transforming the ligation mixtures into (a) AB1154, used for YY1; 1 Matα Ψ+ ura3 trp1 ade2-1 can1-100 lys2-1 met4-1 tyrl; ade2-1, can1-100, lys2-1, and met4-1 are ochre alleles, suppressible by SUP4-o; Ψ+ is a cytoplasmic determinant that enhances suppression [Liebman and Sherman, *J. Bact.* 139, 1068 (1979), Tuite et al., *Proc. Natl. Acad. Sci. U.S.A.* 80, 2824 (1983)]; or into (b) AB1380, used for HY clones; Matα Ψ+ ura3 trp1 ade2-1 can1-100 lys2-1 his5. The yeast DNA, which was derived from strain AB972, was prepared as described by Carle and Olson, *Nucleic Acids Res.* 12, 5647 (1984); the human DNA was derived from the known neuroblastoma cell line NLF. See Schwab et al, *Nature* 305, 245 (1983). Both DNA samples had been prepared as liquid solutions; nevertheless, the average size of the fragments before cleavage exceeded 500 kb. After Sma I digestion, the human sample was size-fractionated on a sucrose gradient. Fractions larger than 40 kb were pooled. For the Sma I digests, 25 μg of source DNA were digested to completion, gently extracted first with phenol then with chloroform, dialyzed against TE8 (10 mM TrisHCl, 1 mM EDTA, pH 8), and concentrated in a Schleicher and Schuell UH 100/1 collodion bag concentrator. Vector DNA was prepared by digesting 50 μg of pYAC2 DNA to completion with Sma I and Bam H1, treating with an excess of calf-intestinal alkaline phosphatase (Boehringer-Mannheim, molecular biology grade), extracting sequentially with phenol and then chloroform, and concentrating by ethanol precipitation; the throwaway Bam H I fragment containing the HIS3 gene was not separated from the other two vector fragments. The ligation reaction was carried out for 12 hr at 15° C. in a volume of 200 μl using 50 units of T4-DNA ligase (Boehringer-Mannheim) in 50 mM TrisHCl, 10 mM MgCl$_2$, 1 mM ATP, pH 7.5; following ligation, the reaction mixture was subjected to sequential extractions with phenol and chloroform and dialyzed against TE8. Half the ligation mixture was transformed into 5×10$^7$ cells, which had been converted to spheroplasts with lyticase, and plated onto 4 100-mm Petri plates using a synthetic spheroplast-regeneration medium lacking uracil [Sherman et al., *Methods in Yeast Genetics,* Cold Spring Harbor Lab., N.Y. (1979)]. The transformation protocol followed procedure also described by Burgers and Percival, *Anal. Biochem.* (1987), in press.

Figure 3B:
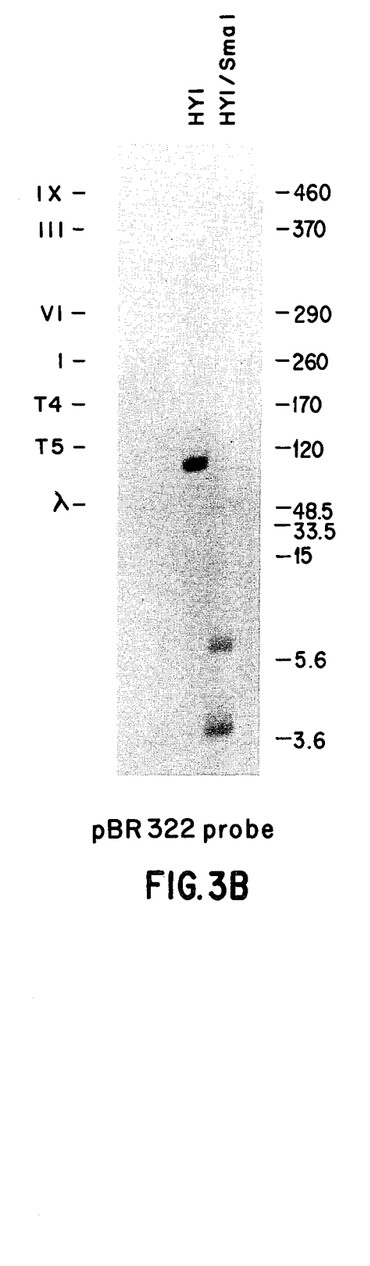
Figure 3C:
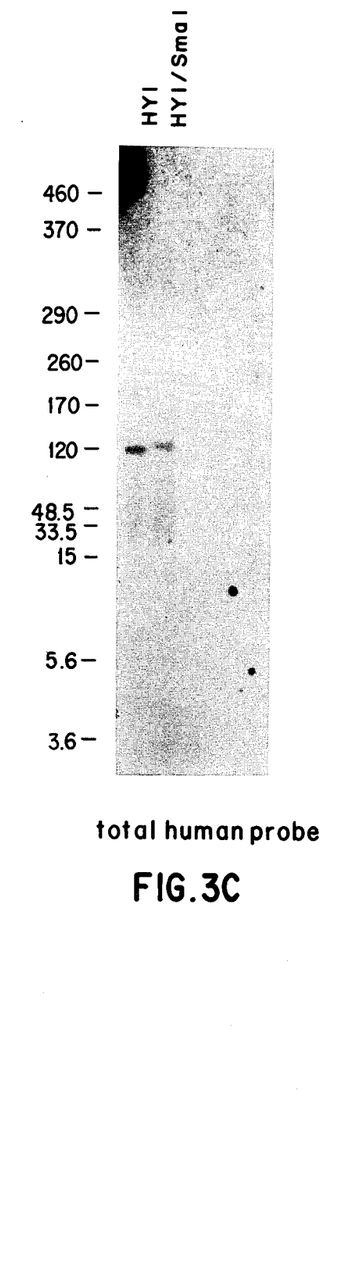

FIG. 3 provides a demonstration that the insert in the Human/Yeast clone HY1 is a single large Sma I fragment. (A) This panel shows an ethidium-bromide-stained gel on which uncleaved and Sma I-cleaved DNA from the transformed yeast strain was fractionated along with size markers (M) in two identical sets of lanes. The high background and absence of intact chromosomes larger than IX (460 kb) in the uncleaved DNA is accounted for by the use of liquid DNA samples [Carle and Olson, *Nucleic Acids Res.* 12, 5647 (1984)] in this test. (B) This panel is an autoradiogram showing that in the uncleaved sample 32P-labeled pBR322 hybridized to intact HY1, while in the Sma I digest it hybridized only to the 5.6 and 3.6-kb arms contributed by pYAC2. The left side of the gel shown in (A) was used in this test; methods were similar to those described for FIG. 2. (C) This panel is an autoradiogram showing that in both the uncleaved and Sma I-cleaved samples, total-human DNA hybridizes to DNA molecules of similar size; in the cleaved sample, the band corresponds to the single human Sma I fragment present as an insert in HY1. The right side of the gel shown in (A) was used in this test.

Figure 4B:
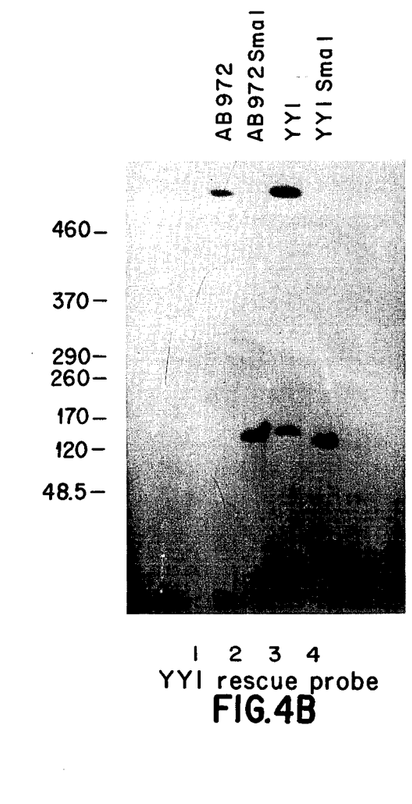

FIG. 4 provides a demonstration that the large yeast Sma I fragment cloned into the Yeast/Yeast clone YY1 is also present in the genome of the yeast strain AB972 from which the source DNA was extracted. (A) This panel shows an ethidium-bromide-stained OFAGE gel on which both uncleaved and Sma I-cleaved DNA from AB972 and the transformed strain containing YY1 has been fractionated (lanes 1–4). The outside lanes on the gel contain size markers. (B) This panel is an autoradiogram showing hybridization of the samples described in (A) to a plasmid probe "rescued" from the insert of YY1 (as described hereinbefore). This probe hybridized in lane 1 to sequences present at the normal chromosomal site of the clone Sma I fragment in AB972; the large hybridizing chromosome was identified as chromosome XII in a separate test. In lane 2, it hybridized to single large Sma I fragment released from chromosome XII of AB972. In lane 3, it hybridized both to the transformation host's chromosome XII and to the YY1 itself. In lane 4, it hybridized to the co-migrating Sma I fragments released from the transformation host's chromosome XII and from YY1.

FIG. 5 shows the indirect-end-label mapping of YY1 with Bam H1. DNA prepared from the transformant containing the artificial chromosome YY1 was subjected to partial digestion with increasing concentrations of Bam H1. The samples were fractionated by field-inversion gel electrophoresis under conditions that maximize resolution in the size range 50–110 kb. The DNA was transferred to nitrocellulose and assayed by hybridization with a probe comprised of vector sequences present at the left end, as defined in FIG. 1, of all YAC clones. The composite map shows the interpretation of the bands in the autoradiogram in terms of BamH I sites in YY1. The correlation between bands and sites requires careful size calibration of the gel since gels of this type display a complex relationship between size and mobility: there is a substantial compression in the range 15–30 kb and a short double-valued region at the top of the gel (molecules of 120 kb have minimal mobility while a heterogeous population of larger molecules comigrate at a slightly higher mobility; there is some non-specific hybridization to the large accumulation of yeast DNA migrating in this high-molecular-weight band). Sites near the right end were mapped in a test identical to that shown except that a probe specific for the right end of YAC clones was employed. The DNA used in these tests was a liquid sample prepared as previously described by Carle and Olson, *Nucleic Acids Res.* 12, 5647 (1984). The electrophoresis conditions involved a voltage gradient of 10.5 volts/cm (measured in the gel), a forward pulse time of 2 sec., a reverse pulse time of 0.667 sec., and a total running time of 12 hr.; other conditions were as described by Carle et al., *Science* 232, 65 (1986). The left-end probe was the larger, and the right-end probe the smaller, of the two fragments produced by double-digestion of pBR322 with Pvu II and Bam H1; both fragments were gel-purified before labeling.

EXAMPLE 2

A limitation on pYAC2 as an all purpose YAC vector is the relative inflexibility of the cloning site. Sma I produces blunt ends, which do not ligate as efficiently as "sticky" ends and also limit the range of ways in which the source DNA can be prepared for cloning. Although a variety of methods exist for overcoming these limitations, they are all more complex than a simple sticky-end ligation and carry the attendant risk of reducing the cloning efficiency. In seeking to adapt YAC vectors to the cloning of fragments generated by a variety of restriction enzymes that leave cohesive ends, the attractive features of SUP4 as an interruptible marker were preserved while circumventing the inflexibility of the coding-region Sma I site. This goal was achieved by moving the cloning site into the gene's 14-bp intron. The need to maintain SUP4 function in the vector was deemed to place few constraints on the intron's sequence or precise length; it was also deemed that the cloning or huge inserts into the intron would still inactivate the gene. Site-directed mutagenesis was used to make a single nucleotide change in the wild-type intron, creating a Sna B1 site that is unique in the vector. In the process of reconstructing a vector that contained the SnaB I site, the Sfi I and Not I sites flanking the SUP4 gene in pYAC2 were eliminated in order to allow these enzymes to be used more conveniently either in preparing source DNA for cloning or in the analysis of clones. In this way, a series of vectors was constructed that offer the following cloning sites: the SnaB I site itself (pYAC3), a unique EcoR I site created by insertion of an EcoR I linker -d(GGAATTCC)- into the SnaB I site (pYAC4), and a similarly constructed unique Not I site (pYAC5). In all cases, these manipulations preserved SUP4 function.

Figure 6:
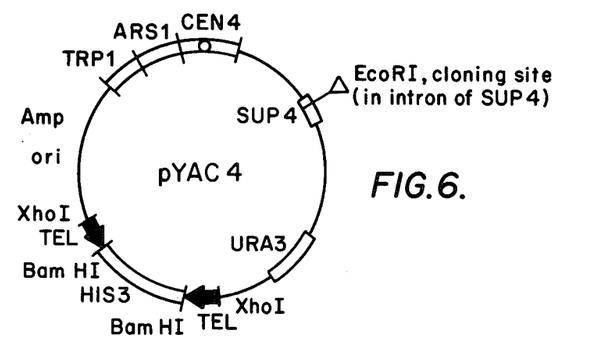
FIG. 6 is a diagrammatic representation which shows the yeast plasmid vector pYAC4 in another embodiment of the invention.
Figure 7:
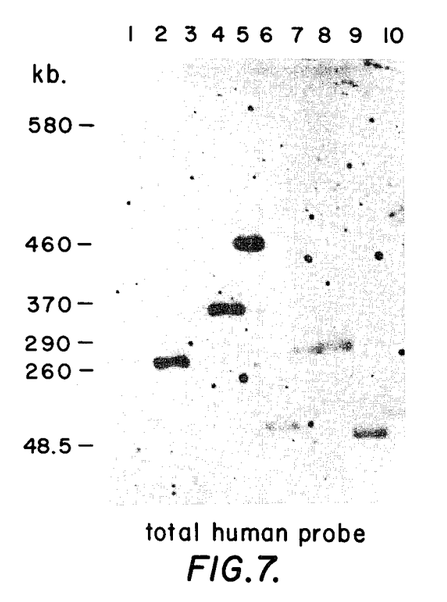
FIG. 7 shows the results of electrophoresis demonstrating the sizing of yeast artificial chromosomes present in ten transformants generated by cloning human DNA fragments into the yeast plasmid vector pYAC4 of FIG. 6.

The most extensively tested of these other vectors is pYAC4, shown in FIG. 6, which allows the direct cloning of inserts produced by EcoR I partial digestion. This vector was tested on a population of EcoR I partial-digest fragments prepared from the DNA of circulating human leukocytes. The uncleaved source DNA had an average size of over 10³ kb, while the partial-digest fragments, which were not size-fractionated, were predominantly in the size range 50–700 kb. In this test, the cloning efficiency was similar to that reported above for pYAC2 cloning (several hundred clones per microgram of source DNA), but the fraction of the primary transformants that had all the phenotypes of bona fide recombinants was much higher (>90%); furthermore, nearly all such colonies contained a single artificial chromosome that hybridized to a total-human probe. FIG. 7 shows these hybridization results for DNA prepared from 10 clones that were picked at random: all 10 clones contain human DNA present in artificial chromosomes ranging in size up to more than 400 kb.

FIG. 7 thus shows the sizing of the artificial chromosomes present in ten transformants generated by cloning EcoR I partial-digest fragments of human DNA into the EcoR I vector pYAC4. DNA from the transformants was prepared in agarose blocks, electrophoresed at a pulse time of 30 sec. on pulsed-field gel apparatus that produces uniform, transverse fields intersecting at 120° [Chu et al., Science 234, 1582 (1986)], transferred to nitro-cellulose and assayed by hybridization with $^{32}$P-labeled human DNA. The design of the cloning test was as described above. The human DNA used for the EcoR I partial digestion was prepared starting from circulating leukocytes using a liquid-sample method whose application to yeast has been described by Carle and Olson, Nucleic Acids Res. 12, 5647 (1984). The average molecular weight of the DNA before partial digestion with EcoR I was approximately 1000 kb; digestion of 40 μg of this sample was carried out using 0.001 units of EcoR I for 15 min. at 25°. Ligation and transformation conditions were as described above with respect to FIG. 1. The transformation host was AB1380.

The foregoing examples indicate that the generation of yeast artificial chromosomes using YAC vectors provides a general method of cloning exogenous DNA fragments of several hundred kilobase pairs. Although only "anonymous" clones have been analyzed, these clones were demonstrated to be propagated as stable, faithful copies of the source DNA. The efficiency with which clones can be generated is ample to allow generation of multi-hit comprehensive libraries of the genomes of higher organisms, particularly in applications in which the availability of source DNA is not limiting. In such situations, the number of clones that can be obtained per Petri plate following transformation is the most relevant measure of practicality; the above protocols with YAC vectors allow the recovery of thousands of clones per plate, a number that compares favorably with the need for $2 \times 10^4$ clones with 150-kb inserts to obtain single-hit coverage of a mammalian genome.

Various other examples will be apparent to the person skilled in the art after reading the present disclosure without departing from the spirit and scope of the invention, and it is intended that all such examples be included within the scope of the appended claims. Thus, other plasmid vectors can be constructed having the general structural components for replication in yeast as defined herein to allow cloning of a variety of large segments of greater than 50 kb of exogenous DNA as yeast artificial chromosomes. So also, similar such plasmid vectors can be constructed in other yeast strains, for example, Saccharomyces carlbergensis, and the like. The plasmid vectors as defined herein also can be constructed to include the requirements designed to facilitate the expression of exogenous protein. For example, the structural gene for exogenous protein can be fused to a host transcriptional control region. When the plasmid containing this hybrid gene is introduced into the host, the exogenous protein will be synthesized. See, for example, expression of the gene for bovine growth hormone in yeast as described in U.S. Pat. No. 4,443,539, and expression of the gene for antithrombin III in yeast as disclosed in U.S. Pat. No. 4,632,981.

What is claimed is:

1. A Saccharomyces yeast artificial chromosome circular vector comprising the DNA sequences of an autonomous replication sequence, a centromere, a selectable yeast marker, two sequences that seed telomere formation in vivo, and a cloning site for insertion of large segments of greater than 50 kb of exogenous DNA within a yeast gene whose interruption is phenotypically visible.

2. A Saccharomyces yeast artificial chromosome circular vector comprising the DNA sequences of an autonomous replication sequence, a centromere, selectable yeast markers on both sides of the centromere, two sequences that seed telomere formation in vivo separated by a throw-away sequence, and a cloning site for insertion of large segments of greater than 50 kb of exogenous DNA within a yeast gene whose interruption is phenotypically visible.

3. The vector of claim 2 in which the yeast gene with the cloning site is SUP4.

4. The vector of claim 3 in which the cloning site is Sma I.

5. The vector of claim 2 in which the selectable yeast markers are TRP1 and URA3.

6. The vector of claim 2 in which the throw-away sequence is HIS3.

7. The vector of claim 2 in which Xho I sites are centromere-proximal to each of the telomere formation sequences.

8. The vector of claim 2 including the origin of DNA replicon (ori) and the ampicillin resistance gene (Amp) of a bacterial plasmid to allow replication in bacteria.

9. The vector of claim 3 in which the cloning site is in the SUP4 gene's basepair intron.

10. The vector of claim 9 in which the cloning site is SnaB I.

11. The vector of claim 10 in which the Sfi I and Not I sites flanking the SUP4 gene are deleted.

12. The vector of claim 10 in which an EcoR I linker is inserted into the SnaB I site.

13. Plasmid pYAC2.

14. Plasmid pYAC4.

15. Sacchromyces cerevisiae cells transformed with the plasmid of claim 13 ligated to a segment of greater than 50 kb of exogenous DNA.

16. Saccharomyces cerevisiae cells transformed with the plasmid of claim 14 ligated to a segment of greater than 50 kb of exogenous DNA.

17. The cells of claim 15 in which the host strain is AB1380.

18. The cells of claim 16 in which the host strain is AB1380.

19. The method of producing a yeast artificial chromosome comprising cleaving a vector as defined in claim 1 with selected restriction endonucleases to form a left chromosome arm including the centromere and the autonomous replication sequence, and a right chromosomal arm, and then ligating said arms onto a large exogenous DNA insert molecule of greater than 50 kb.

20. The method of producing a yeast artificial chromosome comprising cleaving plasmid pYAC2 with BamH I and Sma I restriction endonucleases to form a left chromosome arm including the centromere and the autonomous replication sequence, a right chromosomal arm, and a throw-away sequence, treating said arms with alkaline phosphatase to prevent religation and then ligating said arms onto a large exogenous DNA inset molecule of greater than 50 kb having Sma I compatible ends.

21. The method of producing a yeast artificial chromosome comprising cleaving plasmid pYAC4 with BamH I and EcoR I restriction endonucleases to form a left chromosome arm including the centromere and the autonomous replication sequence, a right chromosomal arm, and a throw-away sequence, treating said arms with alkaline phosphatase to prevent religation and the ligating said arms onto a large exogenous DNA insert molecule of greater than 50 kb having SnaB I compatible ends.

* * * * *